(12) United States Patent
Mortensen

(10) Patent No.: US 6,777,943 B2
(45) Date of Patent: Aug. 17, 2004

(54) METHOD AND APPARATUS FOR MONITORING A CATHODIC PROTECTED STRUCTURE

(75) Inventor: Peter Mortensen, Fredensborg (DK)

(73) Assignee: Mogens Balslev Rådgivende Ingeniører A/S, Glostrup (DK)

( * ) Notice: Subject to any disclaimer, the term of this patent is extended or adjusted under 35 U.S.C. 154(b) by 0 days.

(21) Appl. No.: 10/172,098

(22) Filed: Jun. 13, 2002

(65) Prior Publication Data
US 2002/0167325 A1 Nov. 14, 2002

Related U.S. Application Data

(63) Continuation of application No. PCT/DK00/00692, filed on Dec. 13, 2000.

(30) Foreign Application Priority Data
Dec. 14, 1999 (DK) .......................................... 1999 01789

(51) Int. Cl.[7] .......................... G01N 27/42; G01N 27/02
(52) U.S. Cl. ........................ 324/425; 324/445; 324/444
(58) Field of Search ................................ 324/425, 443, 324/444, 71.3

(56) References Cited

U.S. PATENT DOCUMENTS

| | | |
|---|---|---|
| 4,940,944 A | 7/1990 | Steele et al. ................. 324/425 |
| 5,077,486 A * | 12/1991 | Marson et al. ............... 205/728 |
| 5,216,370 A | 6/1993 | Bushman et al. ............ 324/425 |
| 5,469,048 A | 11/1995 | Donohue .................... 324/71.1 |
| 5,541,459 A | 7/1996 | Jonsson et al. ................ 307/95 |
| 5,999,107 A | 12/1999 | Cooper et al. .......... 340/870.16 |
| 6,160,403 A * | 12/2000 | Kajiyama .................... 324/425 |

FOREIGN PATENT DOCUMENTS

| | | |
|---|---|---|
| DK | 169788 | 11/1991 |
| EP | 0529372 | 3/1993 |
| EP | 0882 975 A1 | 12/1998 |
| ES | 2006797 | 5/1989 |
| SU | 796892 B | 1/1981 |
| SU | 934844 A | 8/1986 |

* cited by examiner

Primary Examiner—N. Le
Assistant Examiner—John Teresinski
(74) Attorney, Agent, or Firm—Winston & Strawn LLP

(57) ABSTRACT

A method and an apparatus for utilizing a periodic disconnection of a cathodic protection circuit, the voltage fluctuations caused on a cathodically protected structure by periodic disconnection of the protection circuit being detected in an apparatus and used for remote-controlled disconnection of a decoupling capacitor. Detection of periodically occurring negative-going voltage edges on a cathodically protected structure. The voltage supply of an apparatus through a capacitor or an electric circuit by means of a current transformer and a voltage outlet via a breaker.

14 Claims, 1 Drawing Sheet

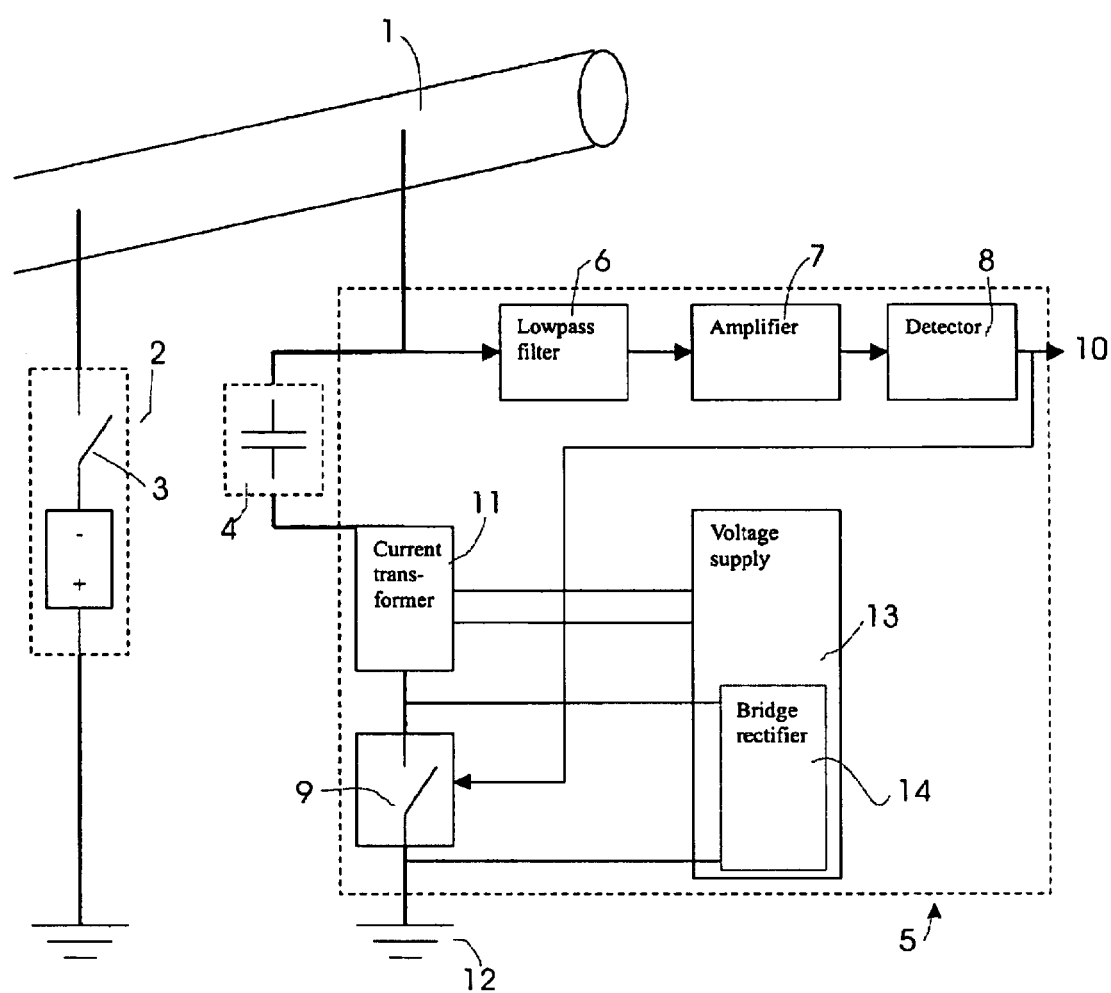

METHOD AND APPARATUS FOR MONITORING A CATHODIC PROTECTED STRUCTURE

CROSS-REFERENCE TO RELATED APPLICATIONS

This application is a continuation of the US national stage designation of International application PCT/DK00/00692 filed Dec. 13, 2000, the content of which is expressly incorporated herein by reference thereto.

BACKGROUND ART

The invention relates to a method and an apparatus for monitoring the protective state of a cathodically protected structure connected to a protection circuit and at least one second electric circuit, whereby the protection circuit is periodically disconnected and the polarized potential of the structure is measured during the disconnected periods.

Buried structures, especially metal structures such as pipelines, will always corrode due to the galvanic activity at the interface between the surface of the pipe and the surrounding soil. In most cases, the corrosion rate can be reduced by displacing the electropotential towards lower values. Normally, this potential displacement is carried out by loading the object to be protected with a cathodic current so that a negative polarization is generated.

One of the problems associated with such cathodic protection systems is the ability to monitor and maintain the protection potential induced on the object.

In connection with the maintenance of cathodically protected structures it is well known to perform measurement of the protective state of the structures by periodically disconnecting the protection circuit with a time switch and by measuring the polarized potential of the structure during the disconnected periods.

This is known, for example, from U.S. Pat. No. 5,999,107, which describes a system for remotely measuring the state of a cathodically protected system by performing measurements and switchings in a control circuit by a wireless remote control. It is also normal to connect electric circuits in the form of decoupling capacitors and overvoltage absorbers to cathodically protected structures with the purpose of diverting induced alternating currents.

However, the polarized potential on a cathodically protected structure cannot be measured as long as decoupling capacitors or similar electric circuits are connected to the structure. It is for this reason that it is necessary to disconnect these electric circuits during the periods when the protective state is to be measured.

On extensive structures, such as gas and oil pipelines, it is very complicated and expensive to disconnect these electric circuits manually each time the polarized potential is to be measured and to reconnect them again after carrying out the measurements. The present invention seeks to overcome this problem is a new and useful manner.

SUMMARY OF THE INVENTION

The present invention provides a method and an apparatus for automatically disconnecting the decoupling capacitors or electric circuits containing the same during the periods when the protection circuit is periodically disconnected by the time switch.

The novel and unique features according to the invention, whereby this is achieved, is the fact that the voltage fluctuations which the periodic disconnections of the protection circuit generate on the cathodically protected structure are detected and that the detected signals are used for controlling the at least one second electric circuit.

Thereby, it is obtained that the maintenance work on extensive cathodically protected structures is facilitated considerably as the detected signals can be used directly for remote-controlling these functions or in replacement of manual work processes by replacing these processes by remote control.

In an especially advantageous method according to the invention, the detected signals are used via a breaker connected in series to the at least one second electric circuit for controlling this circuit. The electric circuit can be connected between the cathodically protected structure and an earthing system, and the signal can advantageously disconnect this connection when the polarized potential of the structure is to be measured.

BRIEF DESCRIPTION OF THE DRAWING

The invention will be explained in greater detail below with reference to the single drawing FIGURE which is a schematic view of an apparatus according to the invention.

DETAILED DESCRIPTION OF PREFERRED EMBODIMENTS

According to the present invention, the apparatus comprises a detection circuit for detecting the voltage fluctuations which the periodic disconnections of the protection circuit generate on the cathodically protected structure, and means for using the detected signals for controlling the at least one second electric circuit.

Advantageously, the means for using the detected signals for controlling the at least one second electric circuit comprise a breaker connected in series to the at least one second electric circuit.

In a preferred embodiment, the detection circuit is arranged to be activated by negative-going edges of the detected signal as these due to the impedance conditions in the protection circuit are more steep than the positive one.

There is normally much electric noise on cathodically protected structures resulting from other electric systems and dominated by 50 Hz with subharmonic and harmonic frequencies.

In certain countries 16⅔ Hz can also occur. The cycle time in the periodic interruption of the protection current is most often seconds, and the frequency content of the voltage fluctuations that occur in this connection on cathodically protected structures is considerably lower than the frequency content of the noise voltages, for which reason the detection circuit advantageously can include a low-pass filter which mainly removes the noise voltages and passes the periodic signals.

Cathodically protected structures are available in very varying sizes, and in connection with the largest ones are often used a large number of decoupling capacitors. This means that the periodic signal can occur with very varying amplitudes and that it therefore is expedient to let the detection circuit comprise a nonlinear amplifier. Thereby, it is obtained that each apparatus according to the invention does not have to be adjusted to the specific application. The nonlinear amplifier must be designed with a relatively high amplification in case of weak input signals and low amplification in case of strong input signals.

It can in some cases be expedient to use an amplifier with Automatic Gain Control (AGC) instead of the nonlinear amplifier.

On cathodically protected structures, aperiodic changes in the potentials occur on rare occasions that could be confused with edges resulting from interruption of the protection circuit, for which reason a frequency detector can be used in an especially advantageous embodiment for detecting the periodic signal. The apparatus can furthermore advantageously comprise a terminal for controlling signals from the frequency detector.

In connection with very extensive cathodically protected structures, it would involve substantial costs to establish traditional power supply to apparatuses according to the invention. The previously mentioned noise voltages can be used as power supply to the apparatus, but in order to avoid affecting the cathodic protection, the power should not be absorbed with any DC content from the cathodically protected structure. This problem can be avoided by the necessary power being drawn through a capacitor.

Often, the circuit which is to be disconnected by means of a method according to the invention will have a capacitive characteristic. Any practical capacitor is characterized by a small but in connection with cathodic protection considerable leakage current. This also applies to the capacitor, for which reason in a particular coupling method with a current transformer the noise voltage passing through the decoupling capacitor is utilized to supplying power to the apparatus when the breaker is closed. When the breaker is open, the power is drawn from the noise voltage which in this situation is across the breaker. Hereby, it is obtained that the apparatus does not contribute with a leakage current by its power absorption but that only the decoupling capacitor is determining for the magnitude of the leakage current.

A structure (1) is protected cathodically by means of a protection circuit (2) which includes a time switch with a switch (3) for periodic disconnection of the protection current. The structure (1) is decoupled through an electric circuit (4) which mainly has a capacitive characteristic.

The invention relates to a method which can be realised by an apparatus (5), the purpose of which is to break the current through the electric circuit (4) when the protective state of the structure (1) is to be measured.

During normal operation, the switch (3) of the time switch is not activated, and the protection circuit is connected to the structure, the switch (3) of the time switch being closed. When the time switch is activated, it opens the protection circuit in a slow cycle, and hereby a slowly pulsating voltage is generated on the structure (1) which together with the present induced noise voltages is carried to the low-pass filter (6) which mainly only passes the slow pulsating voltage. The amplitude of the slow pulsating voltage depends on the point where on the structure (1) the apparatus (5) is connected, and therefore the slow pulsating voltage is carried to an amplifier (7) which can have a nonlinear characteristic or an AGC function in order to ensure that the amplitude after the amplifier is mainly independent of the size of the structure (1) and the location of the apparatus (5) on this structure.

After the amplifier (7), the signal is carried to a detector (8) which detects the relatively steep negative-going edges in the slow pulsating signal. As aperiodic potential changes can occur on the structure (1) with a time lapse which could be confused with a negative-going edge, the detector is designed as a frequency detector which requires a periodic signal to be activated.

The signal of the detector can generally be used for control purposes at a terminal (10), or it can be used specifically for activating a breaker (9) which is opened when a slow pulsating signal is detected by the detector (8).

The apparatus (5) can be supplied with voltage without DC current being drawn from the Structure (1) by connecting the primary of a current transformer (11) in series between the decoupling capacitor (4) and the breaker (9), and by providing the secondary of the current transformer with a bridge connected rectifier (14) in the voltage supply (13). The current transformer (11) will be activated when the breaker (9) is closed. The voltage supply (13) can also absorb power by a bridge connected rectifier connected in parallel over the breaker (9) where most of the noise voltages will be present when the breaker (9) is open.

By means of the series connection, shown in the drawing of the structure (1) in FIG. 1, decoupling capacitor (4), current transformer (11) and the breaker (9) which is ended in the earthing system (12), the desirable function is obtained due to the that only the leakage current in the decoupling capacitor (4) with DC load affects the protection current and it is thereby avoided that the power supply (13) will influence on it.

What is claimed is:

1. A method for monitoring a cathodically protected structure which is connected to a protection circuit and at least one second electric circuit, which comprises:

perodically disconnecting the protection circuit from the structure;

measuring polarized potentials for the structure during periods of time when the protection circuit is disconnected, the periodic disconnection of the protection circuit generating voltage fluctuations on the cathodically protected structure;

detecting the voltage fluctuations as signals; and controlling the at least one second electric circuit utilizing the detected signals to facilitate maintenance work on the cathodically protected structure.

2. The method according to claim 1, which further comprises connecting the detected signals to the at least one second electric circuit via a breaker connected in series.

3. The method of claim 2 which further comprises providing a current transformer to provide current and providing a bridge rectifier in parallel with the breaker.

4. The method of claim 3 which further comprises supplying voltage via a current transformer arranged in series with an electric circuit comprising the breaker and the bridge rectifier arranged in parallel with the breaker.

5. An apparatus for monitoring a cathodically protected structure connected to a protection circuit and at least one second electric circuit, whereby the protection circuit is periodically disconnected for measurement of polarized potentials of the structure, comprising a detection circuit for detecting voltage fluctuations on the cathodically protected structure generated by the periodic disconnection of the protection circuit as signals and control means for using the detected signals for controlling the at least one second electric circuit to facilitate maintenance work on the cathodically protected structure.

6. The apparatus according to claim 5, wherein the control means comprise a breaker which is connected in series to the at least one second electric circuit.

7. The apparatus according to claim 5, wherein the detection circuit is arranged to be activated by negative-going edges of the detected signal.

8. The apparatus according to claim 5, wherein the detection circuit comprises a low-pass filter.

9. The apparatus according to claim 5, wherein the detection circuit comprises a nonlinear amplifier.

10. The apparatus according to claim 5, wherein the detection circuit comprises an amplifier with AGC.

11. The apparatus according to claim 5, wherein the detection circuit comprises a frequency detector for detecting whether a periodic signal is present over a certain period of time.

12. The apparatus according to claim 11, wherein the apparatus comprises a terminal for controlling at least one signal from the frequency detector.

13. The apparatus according to claim 5, wherein the apparatus is arranged to be supplied via a capacitor with voltage from the cathodically protected structure.

14. The apparatus according to claim 5, which is supplied with voltage via a current transformer arranged in series with an electric circuit comprising the breaker and a bridge rectifier arranged in parallel to the breaker.

* * * * *

UNITED STATES PATENT AND TRADEMARK OFFICE
CERTIFICATE OF CORRECTION

PATENT NO. : 6,777,943 B2
DATED : August 17, 2004
INVENTOR(S) : Mortensen

It is certified that error appears in the above-identified patent and that said Letters Patent is hereby corrected as shown below:

Column 4,
Line 25, change "perodically" to -- periodically --.

Signed and Sealed this

Eighth Day of February, 2005

JON W. DUDAS
*Director of the United States Patent and Trademark Office*